(12) United States Patent
Sibik (10) Patent No.: US 9,017,523 B2
(45) Date of Patent: Apr. 28, 2015

(54) PACKED BED SCRUBBER USING A FUSEL OIL SOLVENT

(75) Inventor: Larry Kenneth Sibik, White Bear Lake, MN (US)

(73) Assignee: Pinnacle Engineering, Inc., Maple Grove, MN (US)

( * ) Notice: Subject to any disclaimer, the term of this patent is extended or adjusted under 35 U.S.C. 154(b) by 653 days.

(21) Appl. No.: 13/160,261

(22) Filed: Jun. 14, 2011

(65) Prior Publication Data

US 2012/0214215 A1  Aug. 23, 2012

Related U.S. Application Data

(60) Provisional application No. 61/354,631, filed on Jun. 14, 2010.

(51) Int. Cl.
| | |
|---|---|
| *B01D 3/14* | (2006.01) |
| *B01D 53/78* | (2006.01) |
| *C07C 29/80* | (2006.01) |
| *C07C 31/08* | (2006.01) |
| *B01D 53/14* | (2006.01) |
| *B01D 3/00* | (2006.01) |
| *C12M 1/00* | (2006.01) |
| *C12P 7/06* | (2006.01) |

(52) U.S. Cl.
CPC .......... *B01D 53/1487* (2013.01); *B01D 3/001* (2013.01); *B01D 3/143* (2013.01); *B01D 53/78* (2013.01); *B01D 53/1493* (2013.01); *C07C 29/80* (2013.01); *C07C 31/08* (2013.01); *B01D 53/1406* (2013.01); *B01D 2252/103* (2013.01); *B01D 2252/202* (2013.01); *B01D 2257/70* (2013.01); *C12M 21/12* (2013.01); *C12M 43/02* (2013.01); *C12M 47/18* (2013.01); *C12P 7/06* (2013.01); *Y02E 50/17* (2013.01)

(58) Field of Classification Search
CPC .......... B01D 3/001; B01D 3/14; B01D 3/143; B01D 53/1487; B01D 53/1493; B01D 53/18; B01D 53/78; C07C 7/04; C07C 7/11; C07C 29/80; C07C 31/08; Y02E 50/16; Y02E 50/17
USPC ......... 202/158; 203/19, 42; 95/187, 224, 225, 95/237; 96/243; 261/158, 117; 435/161, 435/291.1; 99/276, 277; 426/11, 14
See application file for complete search history.

(56) References Cited

U.S. PATENT DOCUMENTS

| | | | | |
|---|---|---|---|---|
| 4,358,536 | A * | 11/1982 | Thorsson et al. | ............. 435/161 |
| 4,522,920 | A * | 6/1985 | Thorsson et al. | ............. 435/161 |
| 4,617,270 | A | 10/1986 | Anderson et al. | |
| 4,952,503 | A | 8/1990 | Granstedt | |
| 5,387,322 | A * | 2/1995 | Cialkowski et al. | .......... 202/158 |
| 8,236,535 | B2 * | 8/2012 | Medoff et al. | ................ 435/162 |
| 8,449,728 | B2 * | 5/2013 | Redford | .......................... 203/19 |
| 8,454,802 | B2 * | 6/2013 | Redford | .......................... 203/19 |

(Continued)

FOREIGN PATENT DOCUMENTS

| | | |
|---|---|---|
| GB | 2 223 762 | 4/1990 |
| GB | 2223762 | 4/1990 |

*Primary Examiner* — Nina Bhat
*Assistant Examiner* — Jonathan Miller
(74) *Attorney, Agent, or Firm* — Merchant & Gould PC (57) ABSTRACT

A two stage scrubber process for ethanol fermentation has a first stage using fusel oil to remove the hazardous air pollutants and recover the majority of the ethanol. A second stage uses water as the scrubbing solvent to recover any residual ethanol that is stripped from the first stage.

16 Claims, 9 Drawing Sheets

(56) References Cited

U.S. PATENT DOCUMENTS

| | | |
|---|---|---|
| 8,512,448 B2 * | 8/2013 | Sonnek et al. .................. 95/223 |
| 8,518,683 B2 * | 8/2013 | Medoff et al. ................. 435/177 |
| 8,603,786 B2 * | 12/2013 | Redford ........................ 435/161 |
| 2005/0239181 A1 | 10/2005 | Lewis |
| 2007/0178567 A1 | 8/2007 | Lewis |
| 2008/0135396 A1 | 6/2008 | Blum |
| 2009/0017164 A1 | 1/2009 | Schisler et al. |
| 2009/0263540 A1 | 10/2009 | Allen et al. |
| 2010/0159550 A1 | 6/2010 | Redford |
| 2010/0159551 A1 | 6/2010 | Redford |
| 2011/0108409 A1 * | 5/2011 | Brown ............................ 203/42 |
| 2011/0230394 A1 * | 9/2011 | Wiatr et al. .................... 514/2.4 |

* cited by examiner

PACKED BED SCRUBBER USING A FUSEL OIL SOLVENT

BACKGROUND OF THE INVENTION

1. Field of the Invention

The present invention is directed to an ethanol production system and method and, in particular, to an ethanol production system and method with increased efficiencies through two stage fusel oil scrubbing.

2. Description of the Prior Art

Ethanol production has increased as demand for ethanol has increased. Plants for ethanol production have been developed to meet the demand. Although ethanol provides an alternative energy source and can be blended with other fuels, its production has challenges for efficiencies related to energy consumption, water usage, emission limits and pollution control.

Figure 1:
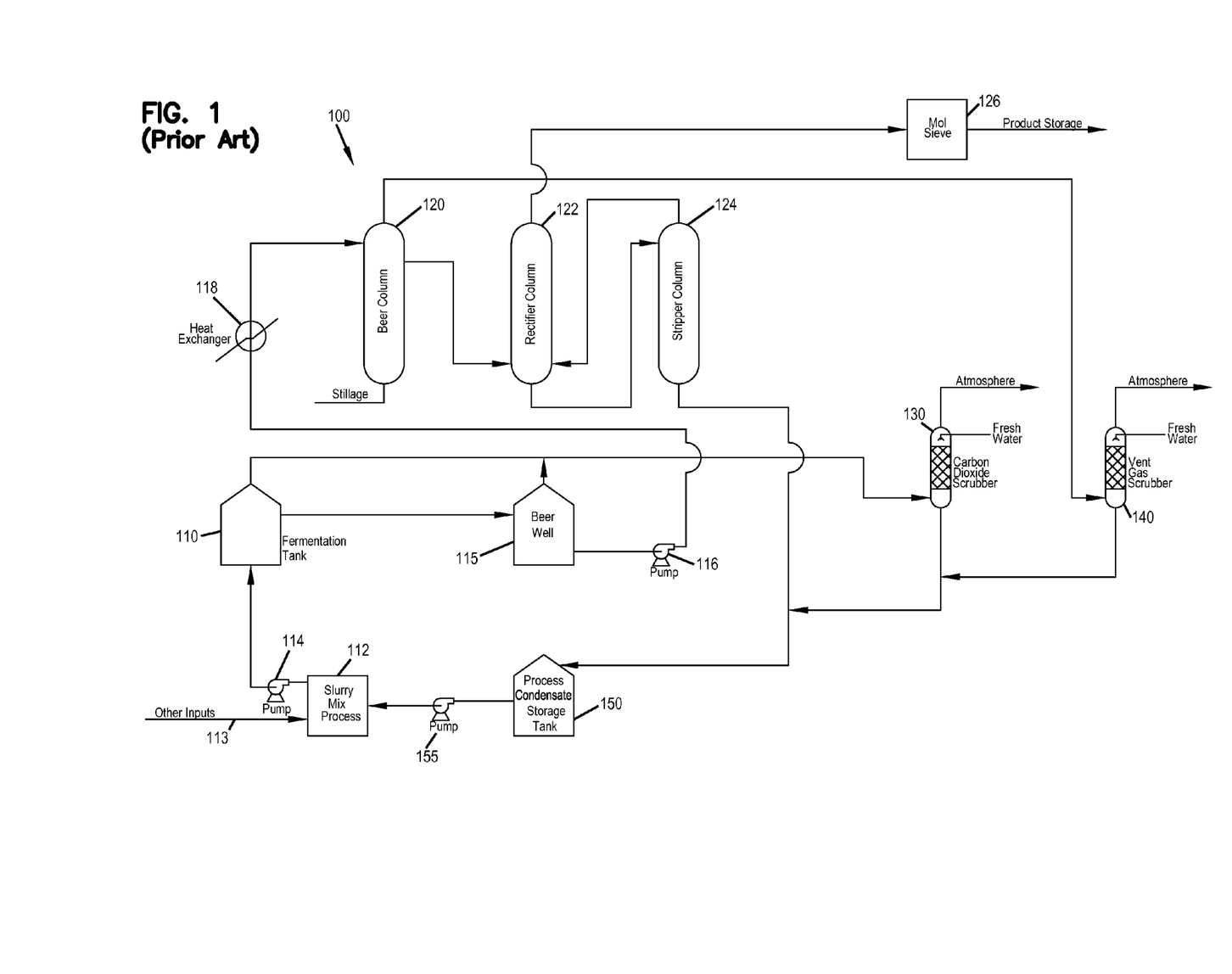
FIG. 1 is a flow diagram of a prior art ethanol production process and system.

FIG. 1 shows an exemplary prior art ethanol production system 100. The system 100 includes a fermentation tank 110, a slurry mix processor 112, and a beer well 115. A starch or cellulose-containing feedstock, such as corn, sorghum, barley, wheat, potatoes, sugar cane, agricultural residues etc, is liquefied in the slurry mix processor 112 by mixing the feedstock with water. Other inputs 113 may be added into the slurry mix processor 112, such as enzymes. A slurry mix pump 114 transports the slurry mix from the slurry mix processor 112 to the fermentation tank 110. The fermentation tank 110 converts sugar contained in the slurry to ethanol using a micro-organism such as yeast. Hazardous air pollutants and a beer product are produced in the fermentation tank 110. The beer product or beer is stored in the beer well 115 prior to distillation.

The exemplary prior art ethanol production system 100 further includes a beer column 120, a rectifier column 122, a stripper column 124, and a molecular sieve 126. Beer stored in the beer well 115 is transported by a beer pump 116 to the beer column 120 via a heat exchanger 118 for increasing the temperature of the beer. The beer column 120 is an initial distillation of ethanol in which solid components or stillage are removed from the liquid components of the beer. The liquid components of the beer are then transported to the rectifier column 122 in which ethanol reaching 95% purity is distilled by further removing water. The 95% ethanol is dehydrated in the molecular sieve 126, e.g. by using a desiccant that captures water molecules and allows ethanol molecules to pass through. The dehydrated ethanol, which may reach 99.4% purity, is then stored. The stripper column 124 is used to remove any residual ethanol from the bottoms of the rectifier column 122. This ethanol and water mixture is returned to the rectifier column 122.

The system 100 further includes a $CO_2$ scrubber 130 and a vent gas scrubber 140. The air pollutants produced during fermentation are processed in the $CO_2$ scrubber 130 using fresh water as scrubber solvent. The $CO_2$ scrubber also captures ethanol vapors and mists that are returned to the process through the process condensate storage tank. The cleaned emissions are released into the atmosphere and water slurry is returned to the process to the slurry mix processor 112 via a process condensate storage tank 150 and a pump 155. Vent gas from the beer column 120 is processed in the vent gas scrubber 140, in which the vent gas is scrubbed with fresh water. The cleaned gas is released into the atmosphere and the water slurry is returned to the slurry mix processor 112 via the process condensate storage tank 150 and the pump 155.

As shown in FIG. 1, some ethanol production processes return a portion of the ethanol produced to the beginning stage of the process. As much as 0.5% ethanol has been reported in water entering the fermentation process. By returning the ethanol to the start of the process, the energy that is used to advance the ethanol through the distillation process is forfeited, leading to inefficiencies. Moreover, the fermentation process is limited by the toxicity posed by ethanol to the yeast in the fermentation process. As the concentration of ethanol increases, up to a typical maximum yield of 15%-18%, the yeast will begin to die off. This may have the effect of essentially adding ethanol back into the start of the production process, thereby limiting the production capacity of the facility.

Other issues arise with the control of acetaldehyde. To control the amount of acetaldehyde created and minimize hazardous air pollutants, sodium bisulfate or ammonium bisulfate has been used to increase the solubility of the acetaldehyde in the scrubber water. The addition of these substances has increased control from an initial 10%-30% solubility by up to 50%-70% solubility. The use of bisulfate additives in the $CO_2$ scrubber has been linked to high sulfate concentrations in the dehydrated ethanol. The sulfate concentration of dehydrated ethanol is limited by the customers of the dehydrated ethanol It can be seen that a need exists to improve the efficiency of ethanol production. Moreover, such a system and process should capture and control hazardous air pollutants emitted from the process, increase production capacity and energy efficiency, eliminate the use of bisulfate scrubber additives and thereby reduce sulfate concentration in the dehydrated ethanol product. The present invention addresses these as well as other problems associated with ethanol production.

SUMMARY OF THE INVENTION

The disclosure is generally directed to an ethanol production system. In one possible configuration and by non-limiting example, the invention relates to a two stage packed bed scrubber system for the recovery of ethanol and the control of hazardous air pollutants. The first stage of the scrubber uses a fusel oil, water and ethanol blend as a scrubbing solvent. The second stage uses water to recover any ethanol that is stripped from the first stage. Both stages recycle the scrubbing solvent.

One aspect of the invention is an ethanol production system including a fermenter in which a mashed feedstock is fermented into a beer product and air pollutants. The system also includes a distillation column configured to distill the beer product into ethanol. The system further has a first scrubber configured to remove the air pollutants produced during fermentation using a scrubber solvent including fusel oils tapped from the distillation column and a second scrubber arranged downstream of the first scrubber and configured to recover ethanol stripped in the first scrubber using water as a scrubber solvent.

Another aspect is a method of recovering ethanol from fusel oils in an ethanol production process. The method includes the steps of fermenting a mashed feedstock, wherein the fermentation process produces a beer product and air pollutants and distilling the beer product into ethanol. The method further includes the steps of tapping fusel oils from the distillation step and using the tapped fusel oils in a first scrubber to remove the air pollutants produced during the fermentation step. The method also includes the step of recovering ethanol stripped in the first scrubber in a second scrubber using water.

Thanks to the provision of an ethanol production system and process in which a two stage scrubber system recovering ethanol is used, an increased efficiency of the ethanol production is obtained.

Some prior art ethanol production facilities have problems with achieving sulfate concentration specified by their customers. By using fuel oil as a scrubbing solvent, the present invention allows these facilities to reduce the concentration of sulfate in the dehydrated ethanol product.

By recovering the majority of the ethanol vapors and mists from the fermentation cycle in the first stage scrubber, the concentration of the ethanol in the scrubbing solvent is increased. The higher concentration of ethanol allows this scrubber water to be moved forward in the distillation and dehydration processes, rather than returned to the start of the fermentation stage.

By recycling water in the second stage scrubber, the amount of water used is greatly reduced to address problems at some prior art ethanol facilities related to maintaining a water balance.

These features of novelty and various other advantages that characterize the invention are pointed out with particularity in the claims annexed hereto and forming a part hereof. However, for a better understanding of the invention, its advantages, and the objects obtained by its use, reference should be made to the drawings that form a further part hereof, and to the accompanying descriptive matter, in which there is illustrated and described a preferred embodiment of the invention.

BRIEF DESCRIPTION OF THE DRAWINGS

Referring now to the drawings, wherein like reference letters and numerals indicate corresponding structure throughout the several views.

DETAILED DESCRIPTION OF THE PREFERRED EMBODIMENT

Figure 2:
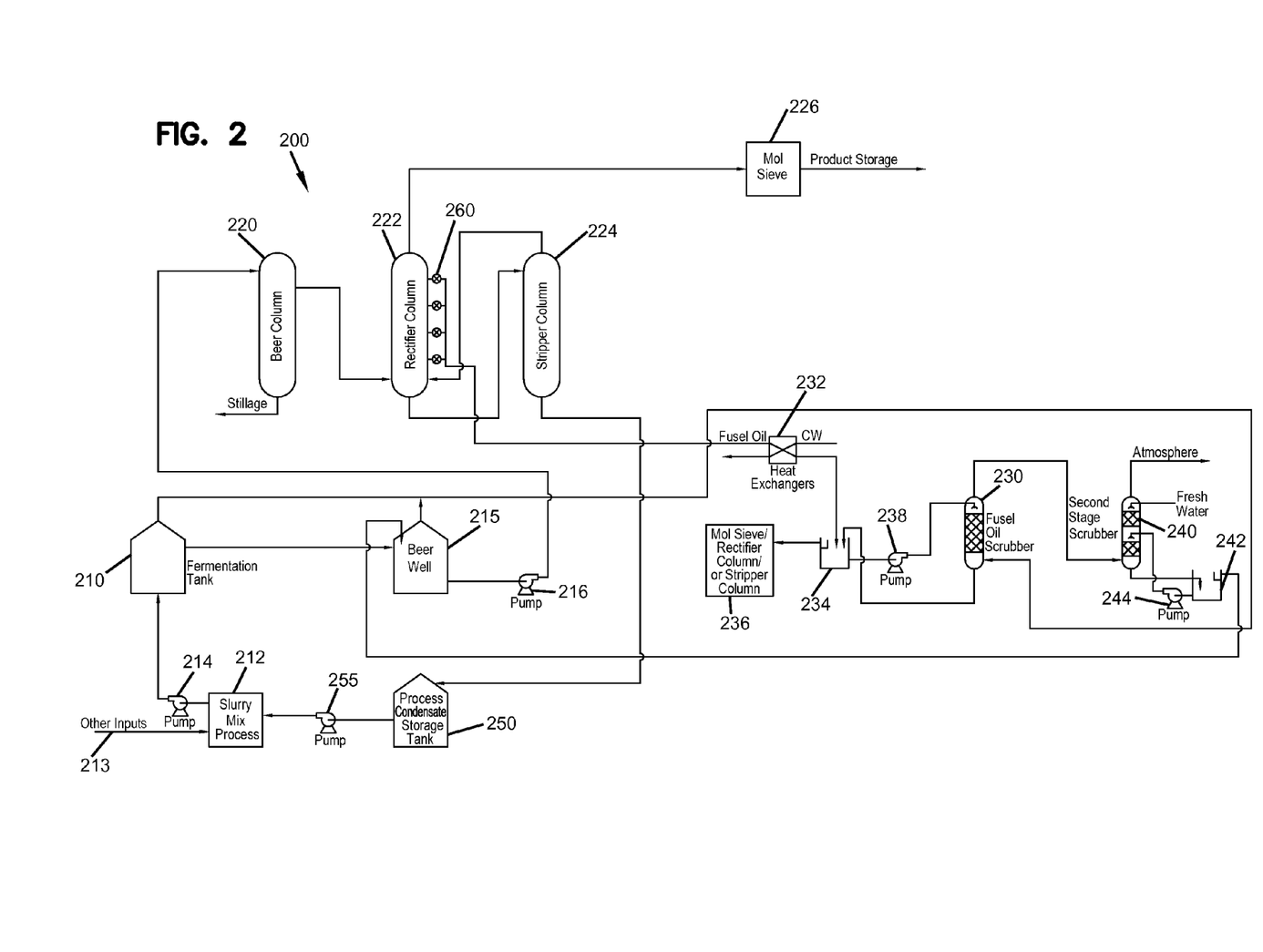
FIG. 2 is a flow diagram of an ethanol production system and method using a fusel oil scrubber according to the principles of the present invention.

Referring now to the drawings and in particular to FIG. 2, there is shown a first exemplary embodiment of an ethanol production system according to the present invention, generally designated 200. The system 200 includes a fermentation tank 210, a slurry mix processor 212, and a beer well 215. A starch or cellulose-containing feedstock, such as corn, sorghum, barley, wheat, potatoes, sugar cane, agricultural residues etc, is liquefied in the slurry mix processor 212 by mixing the feedstock with water. Other inputs 213 may be added into the slurry mix processor 212, such as enzymes. A slurry mix pump 214 transports the slurry mix from the slurry mix processor 212 to the fermentation tank 210. The fermentation tank 210 converts sugar contained in the slurry to ethanol using a micro-organism such as yeast. Hazardous air pollutants and a beer product are produced in the fermentation tank 210. The beer product or beer is stored in the beer well 215 prior to distillation.

The exemplary ethanol production system 200 further includes a beer column 220, a rectifier column 222, a stripper column 224, and a molecular sieve 226. Beer stored in the beer well 215 is transported by a beer pump 216 to the beer column 220. The beer column 220 is an initial distillation of ethanol in which solid components or stillage are removed from the liquid components of the beer. The liquid components from the top of the beer column 220 then flow to the rectifier column 222 in which ethanol reaching 95% purity is distilled by further removing water. Other by-products including fusel oil are also produced in the rectifier column 222. The 95% ethanol is dehydrated in the molecular sieve 226, e.g. by using a desiccant that captures water molecules and allows ethanol molecules to pass through. The dehydrated ethanol, which may reach 99.4% purity, is then stored for usage and/or transport. The stripper column 224 is used to remove any residual ethanol from the bottom of the rectifier column 222. This ethanol and water mixture is returned to the rectifier column 222.

The ethanol production system 200 of the present invention also includes a first fusel oil scrubber 230 and a second stage scrubber 240. During the ethanol distillation process, fusel oils can become trapped in the rectifier column 222. Fusel oil is a by-product of the fermentation process. Fusel oil is composed of higher molecular weight alcohols. The compounds mainly referred to as fusel oils include:

a. 1-propanol;
b. 2-propanol;
c. Butanol;
d. Amyl alcohol; and
e. Furfural.

Because of their physical properties, fusel oils can become trapped in the rectifier column 222 of the ethanol distillation process. Fusel oils need to be periodically tapped at various locations along the middle of the rectifier column 222, as indicated by valves 260. Four valves 260 are shown in FIG. 2, but any number of valves may be used in order to be able to tap the trapped fusel oils. When fusel oils are tapped, water and ethanol are also removed. The present invention provides a use for this by-product in the distillation process.

As can be seen in FIG. 2, the present invention uses a two stage scrubber process. A heat exchanger 232 decreases the temperature of the fusel oils drawn from the rectifier column 222. The cooling of the fusel oil below the boiling point of the acetaldehyde decreases the likelihood that it will be stripped from the fusel oil scrubbing solvent while the solvent is being recycled in the first stage scrubber. The fusel oils are then fed to a tank 234. The system 200 also includes molecular sieve/rectifier column or stripper column 236 to treat product from the tank 234. The molecular sieve/rectifier column or stripper column 236 is shown for simplicity as a separate unit of the system 200 in FIG. 2, but typically the molecular sieve 226, rectifier column 222 and stripper column 224 are used to treat the product from the tank 234. In the first stage, the hazardous air pollutants produced in the fermentation tank 210 are removed in the fusel oil scrubber 230 using fusel oils fed from the tank 234 by a pump 238 as scrubbing solvent. In addition to fusel oils, the scrubber solvent also includes water and ethanol, and in the first stage scrubber a majority of the ethanol is recovered. The scrubber solvent, i.e. fusel oil, ethanol and water, is recycled back to the tank 238.

It has been found that hazardous air pollutants such as acetaldehyde are more soluble in fusel oil than in water. Analytical testing to determine the vapor/liquid equilibrium between the fusel oil and acetaldehyde has shown that the fusel oil scrubbing solvent has the ability to absorb up to 99% of the acetaldehyde. Water based scrubbers typically achieve between 10% and 30% removal of acetaldehyde. The addition of sodium bisulfite or ammonium bisulfite can increase acetaldehyde control to between 50% to 70%. The use of the fusel oil solvent eliminates the use of bisulfite additives, which have been linked to high sulfate levels in the final dehydrated ethanol product. The present invention eliminates the use of bisulfates for scrubber applications and reduces the concentration of sulfate in the dehydrated ethanol products. Some ethanol production facilities have problems with achieving the sulfate concentration specified by their customers. The present invention allows these facilities to reduce sulfate concentration in the dehydrated ethanol product.

In the second stage, any residual ethanol that is stripped from the first stage is recovered in the second scrubber 240 using water as a scrubbing solvent. The cleaned emissions are released into the atmosphere and the recovered ethanol is stored in a tank 242 together with the water used as scrubbing solvent. The second scrubber 240 uses a recycle loop, wherein water/ethanol stored in the tank 242 is pumped back by a pump 244 into the second scrubber 240. The second scrubber 240 uses a recycle loop to decrease the amount of water used, thereby reducing or eliminating water imbalance.

The use of the recycled scrubbing solvent also increases the concentration of ethanol in the scrubbing solvents. Increased concentration of ethanol in the scrubbing solvent allows the solvent to be moved forward in the distillation process, reducing lost energy. As can be seen in FIG. 2, the recovered ethanol stored in the tank 242 is recycled back to the distillation and dehydration process. According to some embodiments, the recovered ethanol is recycled back to the process after the fermenting process, such as to the beer well 215. Some prior art ethanol facilities use a scrubbing solvent, mainly water, in the fermentation process. This procedure returns ethanol back to the start of the production process. As much as 0.5% ethanol has been reported in the water entering the fermentation process. By returning the ethanol to the start of the process, the energy that was used to advance the ethanol through the distillation process is forfeited. Also, the fermentation process is limited by the toxicity posed by ethanol to the yeast in the fermentation process. As the concentration of ethanol increases, typically to a maximum yield of 15-18%, the yeast begins to die off. In effect, adding ethanol back into the start of the production process limits the production capacity of the facility. By increasing the concentration of the ethanol in the scrubbing solvent, it can be moved forward in the distillation and dehydration process to after the fermentation tank 210, such as to the beer well 215. In some embodiments, the recovered ethanol is recycled to other points after the fermenting process than the beer well 215, such as to the beer column 220 or rectifier column 222.

Figure 3:
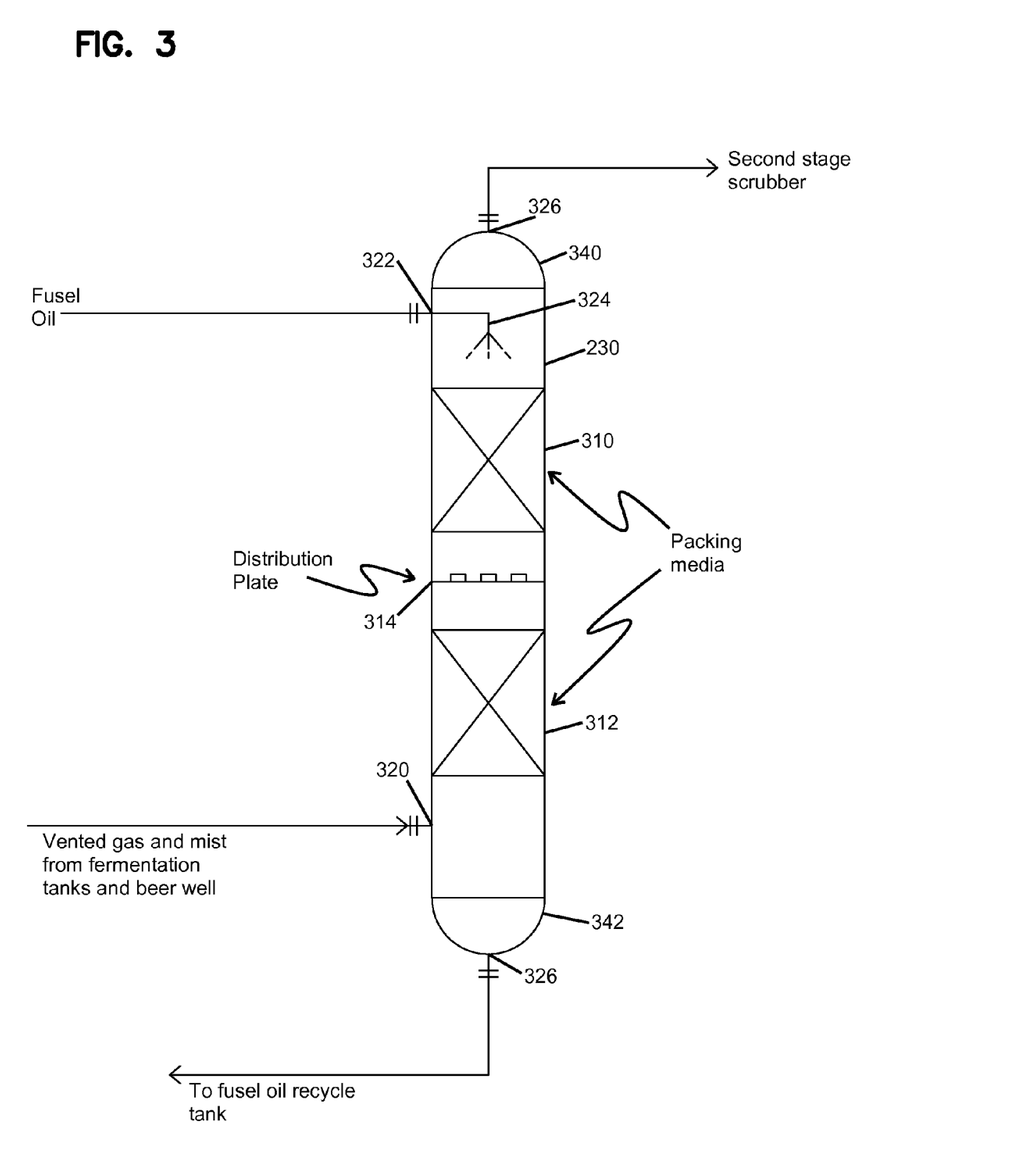
FIG. 3 is an exemplary first stage scrubber.

FIG. 3 shows an exemplary first scrubber 230 of the ethanol production system 200. The first scrubber 230 includes an upper packed bed 310 and a lower packed bed 312 each having packing media which may be randomly dumped or structured in the bed depending on the use of the scrubber 230. Examples of packing media that may be used include rasching rings, berl saddles, intalox saddles, and drip-point grid tiles. The packed beds 310 and 312 are held in place by a packing support and a bed limiter may be used to hold down the top of the packing. The first scrubber 230 further includes a distribution plate 314 arranged between the upper packed bed 310 and the lower packed bed 312. The distribution plate 314 is used to re-distribute the scrubbing solvent, which in the present invention is fusel oil, that has traveled through the upper packed bed 310 to ensure adequate wetting of the lower packed bed 312.

Vented gas and mist from the fermentation tank 210 and the beer well 215 are entering the first scrubber 230 at an inlet 320. Fusel oil tapped from the rectifier column 222 enters the first scrubber 230 through inlet 322 and is sprayed over the upper packed bed 310 through a nozzle 324. Air pollutants in the gas are removed as the gas flows upwards through the packed beds 310 and 312 while the fusel oil flows downward through the packed beds 310 and 312 in countercurrent flow pattern. Air, carbon dioxide and some ethanol leave the first scrubber 230 from an outlet 326 at a top 340 of the first scrubber 230 and are transferred to the second scrubber 240. Fusel oil is collected at a bottom 342 of the first scrubber 230 and is returned through an outlet 326 back to the fusel oil tank 238. As discussed above, the first scrubber 230 shown in FIG. 3 uses a countercurrent flow pattern. However, in some embodiments the first scrubber 230 is configured to use a co-current flow pattern, a perpendicular or cross-flow pattern, or any other know flow patterns instead.

Figure 4:
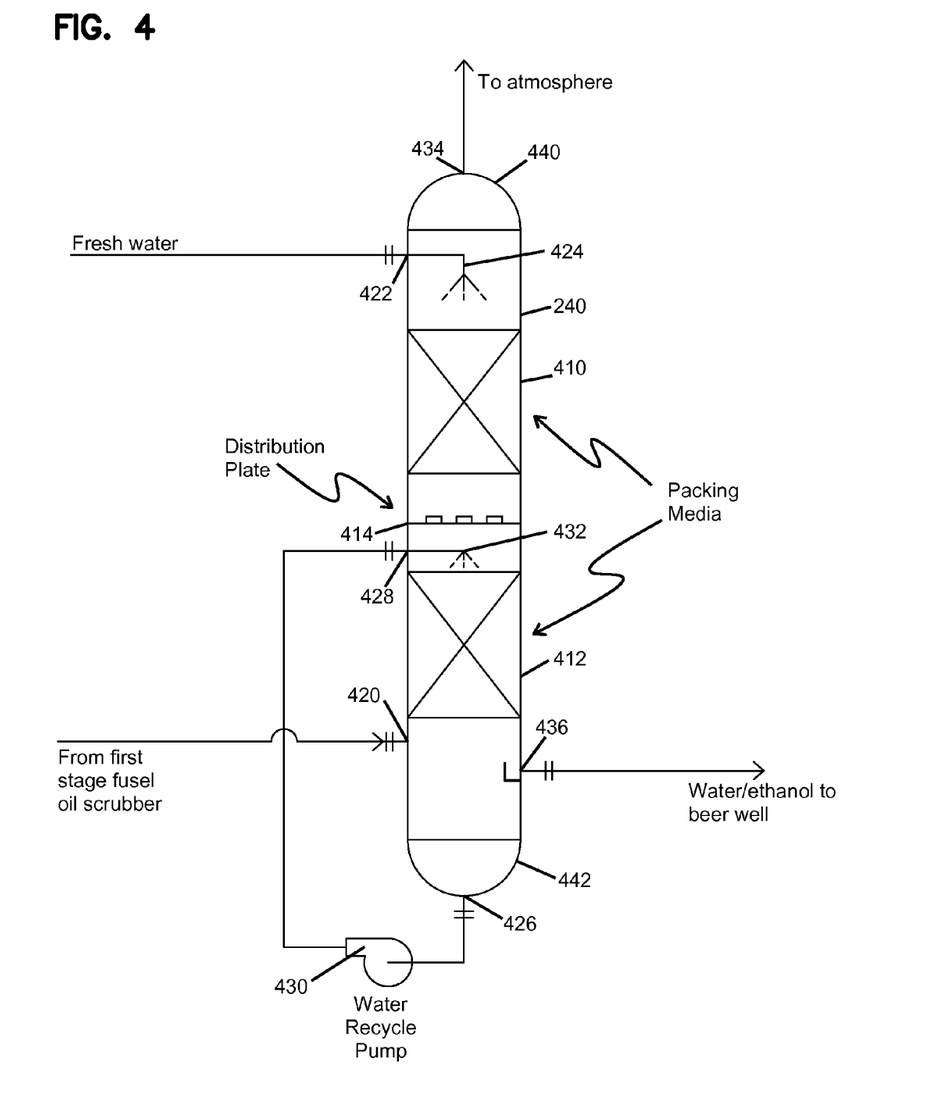
FIG. 4 is an exemplary second stage scrubber.

FIG. 4 shows an exemplary second scrubber 240 of the ethanol production system 200. The second scrubber 240 includes an upper packed bed 410 and a lower packed bed 412 each comprising packing media which may be randomly dumped or structured in the bed depending on the use of the scrubber 240. Examples of packing media that may be used are rasching rings, berl saddles, intalox saddles, and drip-point grid tiles. The packed beds 410 and 412 are held in place by a packing support and a bed limiter may be used to hold down the top of the packing. The first scrubber 240 further includes a distribution plate 414 arranged between the upper packed bed 410 and the lower packed bed 412. The distribution plate 414 is used to re-distribute the scrubbing solvent, which in the present invention is water, that has traveled through the upper packed bed 410 to ensure adequate wetting of the lower packed bed 412.

Air, carbon dioxide and some ethanol from the first scrubber 230 enter the second scrubber 240 at an inlet 420. Fresh water enters the second scrubber 240 through inlet 422 and is sprayed over the upper packed bed 410 through a nozzle 424. Water that has been used as scrubbing solvent is collected on a bottom 442 of the second scrubber 240 and is recycled into the second scrubber 240 by exiting the second scrubber 240 through an outlet 426 at the bottom 442 of the second scrubber 240 via a pump 430 and through an inlet 428 located between the upper packed bed 410 and the lower packed bed 412. The recycled water is sprayed over the lower packed bed 412 through a nozzle 432 and is added to the water that has been re-distributed by the distribution plate 414. As air, carbon dioxide and ethanol flows upward through the packed beds 410 and 412 while the water flows downward through the packed beds 410 and 412 in a countercurrent flow pattern, the ethanol coming from the first scrubber 230 is recovered. Air, carbon dioxide and very little ethanol leave the second scrubber 240 from an outlet 434 at a top 440 of the second scrubber 240 and are released into the atmosphere. The recovered ethanol and water are returned into the ethanol production process through an outlet 436, for example, back to the beer well 215. As discussed above, the second scrubber 240 shown in FIG. 4 uses a countercurrent flow pattern. However, in some embodiments the second scrubber 240 is configured to use a co-current flow pattern or a perpendicular or cross-flow pattern instead.

Figure 5:
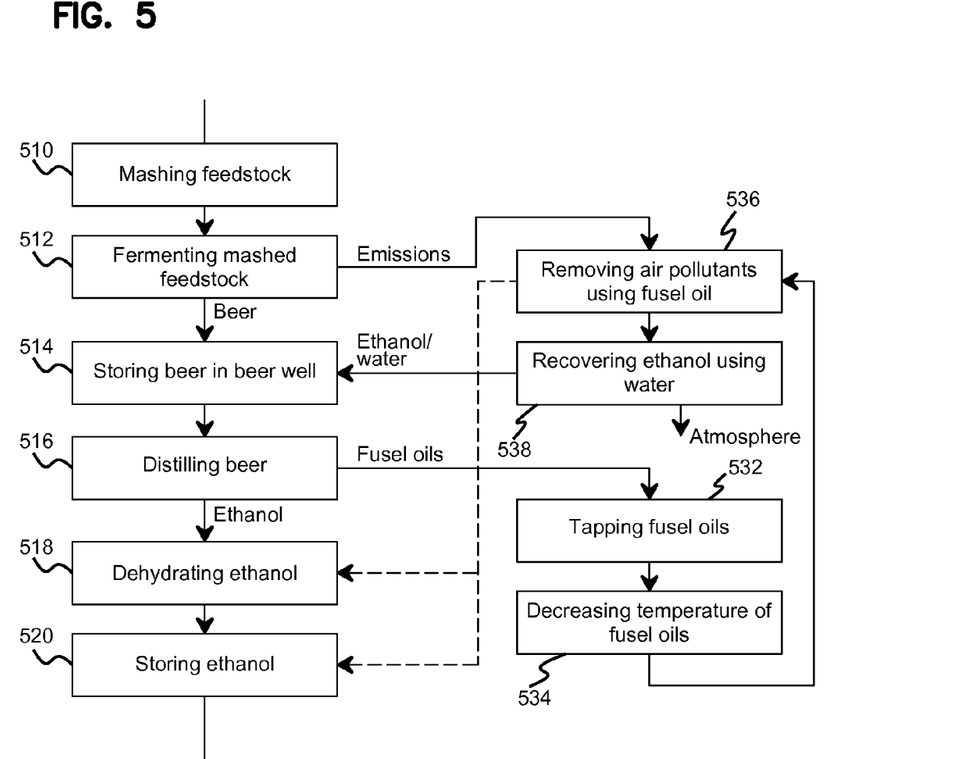
FIG. 5 is a flowchart of an ethanol production process according to a first exemplary embodiment of the present invention.

According to a first embodiment of the present invention, a procedure of producing ethanol, as shown in FIG. 5, is as follows:

mashing feedstock, such as corn, sorghum, barley, wheat, potatoes, sugar cane, agricultural residues etc, by mixing the feedstock with water and other inputs, such as enzymes (step 510);

fermenting the mashed feedstock by adding, for example, yeast (step 512). A beer product and hazardous air pollutants are produced in the fermentation process;

storing the beer product in the beer well 215 (step 514);

distilling the beer into ethanol (step 516) reaching 95% purity in the rectifier column 222. Other by-products including fusel oils are also isolated in the rectifier column 222;

dehydrating the ethanol (step 518) into 99.4% ethanol in the molecular sieve 226, for example by using a desiccant;

storing the ethanol for usage and/or transport (step 520);

tapping fusel oil produced and trapped in the rectifier column 222 (step 532). Ethanol and water are also tapped together with the fusel oil;

decreasing the temperature of the tapped fusel oil blend in the heat exchanger 232 (step 534);

removing air pollutants produced under the fermentation process in the first scrubber 230 using the tapped fusel oil blend as scrubber solvent (step 536). In some embodiments, the fusel oil blend is being moved forward in the process, such as to the step of dehydrating the ethanol, i.e. to the molecular sieve 226. In some embodiments the fusel oil blend is being moved forward to the step of storing the ethanol when there is not too much water in the blend. These embodiments are illustrated in FIG. 5 with the dashed arrows;

recovering ethanol using water as scrubbing solvent in the second scrubber 240 (step 338). The cleaned emissions are released into the atmosphere. The recovered ethanol blended with water is recycled into the process after the fermentation process, such as to the step of storing the beer in the beer well 215.

Figure 6:
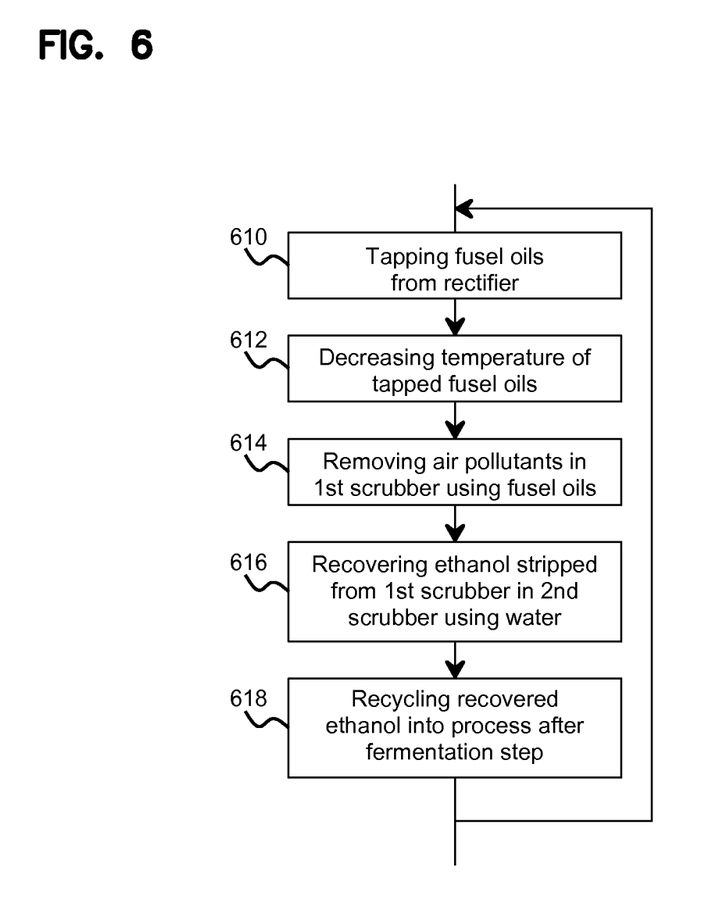
FIG. 6 is a flowchart of an ethanol recovery process according to the first exemplary embodiment of the present invention.

According to the first embodiment of the present invention, a procedure of recovering ethanol from fusel oils in an ethanol production process, as shown in FIG. 6, is as follows:

tapping fusel oil produced and trapped in the rectifier column 222 (step 610). Ethanol and water are also tapped together with the fusel oil;

decreasing the temperature of the tapped fusel oil blend in the heat exchanger 232 (step 612);

removing air pollutants produced under the fermentation process in the first scrubber 230 using the tapped fusel oil blend as scrubber solvent (step 614);

recovering ethanol using water as scrubbing solvent in the second scrubber 240 (step 616);

recycling the recovered ethanol into the process after the fermentation process (step 618), such as into the beer well 215.

Figure 7:
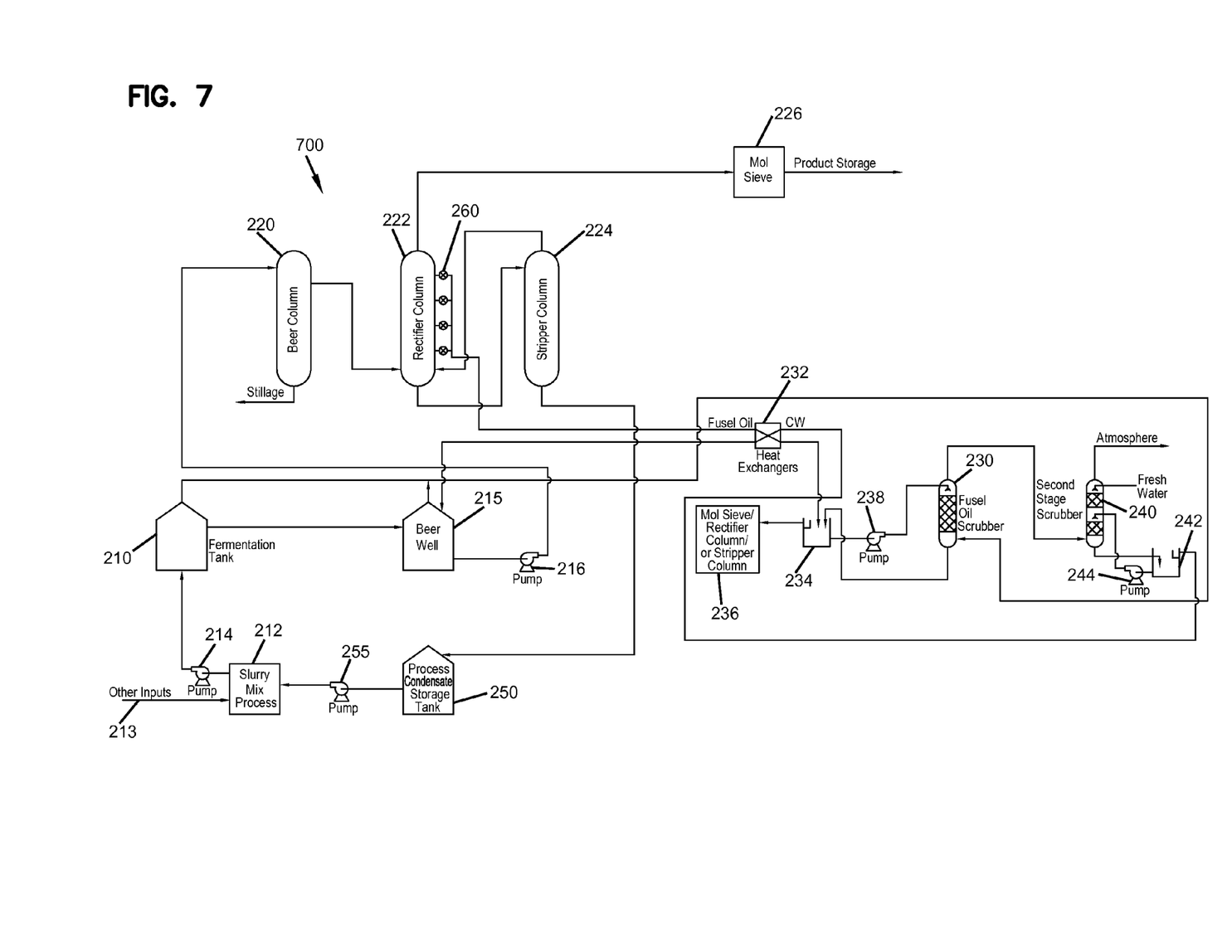
FIG. 7 is a flow diagram of an ethanol production system and method using a fusel oil scrubber according to a second embodiment of the present invention.

FIG. 7 shows a second exemplary embodiment of an ethanol production system according to the present invention, generally designated 700. The system 700 is configured in the same manner as the first exemplary ethanol production system shown in FIG. 2. However, as shown in FIG. 7, the system 700 according to the second embodiment uses the recycled ethanol/water mix in the heat exchanger 232 to decrease the temperature of the tapped fusel oil blend and to increase the temperature of the ethanol/water mix. This heat exchange step has the dual benefit of cooling the fusel oil to below the boiling point of acetaldehyde and heating the alcohol/water mix for prior to entering the beer column.

Figure 8:
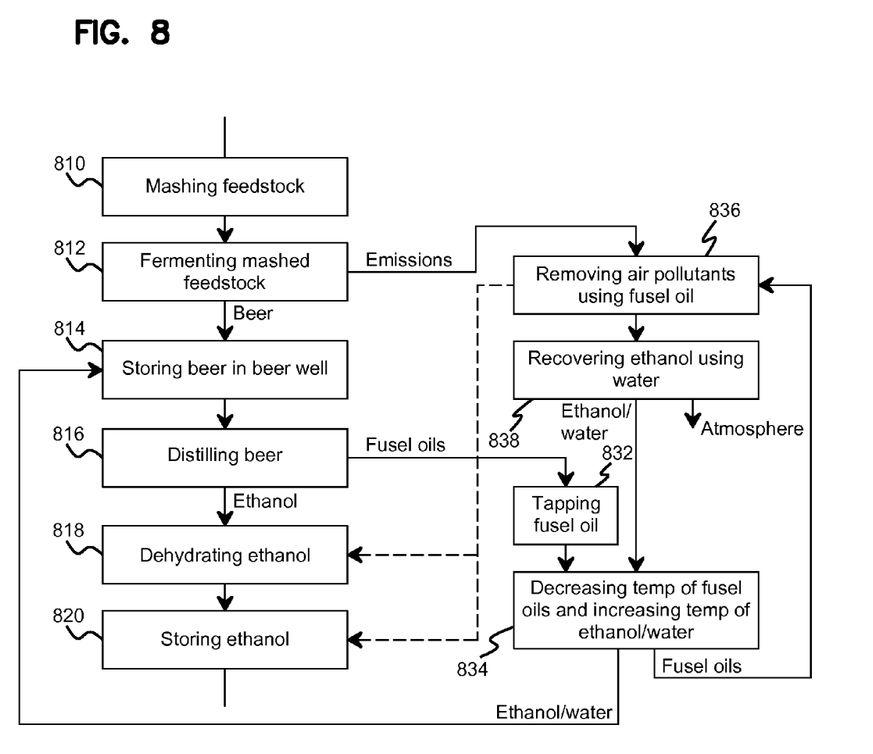
FIG. 8 is a flowchart of an ethanol production process according to the second exemplary embodiment of the present invention.

According to the second embodiment of the present invention, a procedure of producing ethanol, as shown in FIG. 8, is as follows:

mashing feedstock, such as corn, sorghum, barley, wheat, potatoes, sugar cane, agricultural residues etc, by mixing the feedstock with water and other inputs, such as enzymes (step 810);

fermenting the mashed feedstock by adding, for example, yeast (step 812). A beer product and hazardous air pollutants are produced in the fermentation process;

storing the beer product in the beer well 215 (step 814);

distilling the beer into ethanol (step 816) reaching 95% purity in the rectifier column 222. Other by-products including fusel oils are also produced in the rectifier column 222;

dehydrating the ethanol (step 818) into 99.4% ethanol in the molecular sieve 226, for example by using a desiccant;

storing the ethanol for usage and/or transport (step 820);

tapping fusel oil produced and trapped in the rectifier column 222 (step 832). Ethanol and water are also tapped together with the fusel oil;

decreasing the temperature of the tapped fusel oil blend in the heat exchanger 232 (step 834);

removing air pollutants produced under the fermentation process in the first scrubber 230 using the tapped fusel oil blend as scrubber solvent (step 836). In some embodiments, the fusel oil blend is being moved forward in the process, such as to the step of dehydrating the ethanol, i.e. to the molecular sieve 226. In some embodiments the fusel oil blend is being moved forward to the step of storing the ethanol when there is not too much water in the blend. These embodiments are illustrated in FIG. 8 with the dashed arrows;

recovering ethanol using water as scrubbing solvent in the second scrubber 240 (step 838). The cleaned emissions are released into the atmosphere. The recovered ethanol blended with water is used in the heat exchanger 232 to decrease the temperature of the tapped fusel oils in step 834, which increases the temperature of the recovered ethanol/water mix. The recovered ethanol/water mix is then recycled into the process after the fermentation process, such as to the step 814 of storing the beer in the beer well 215.

Figure 9:
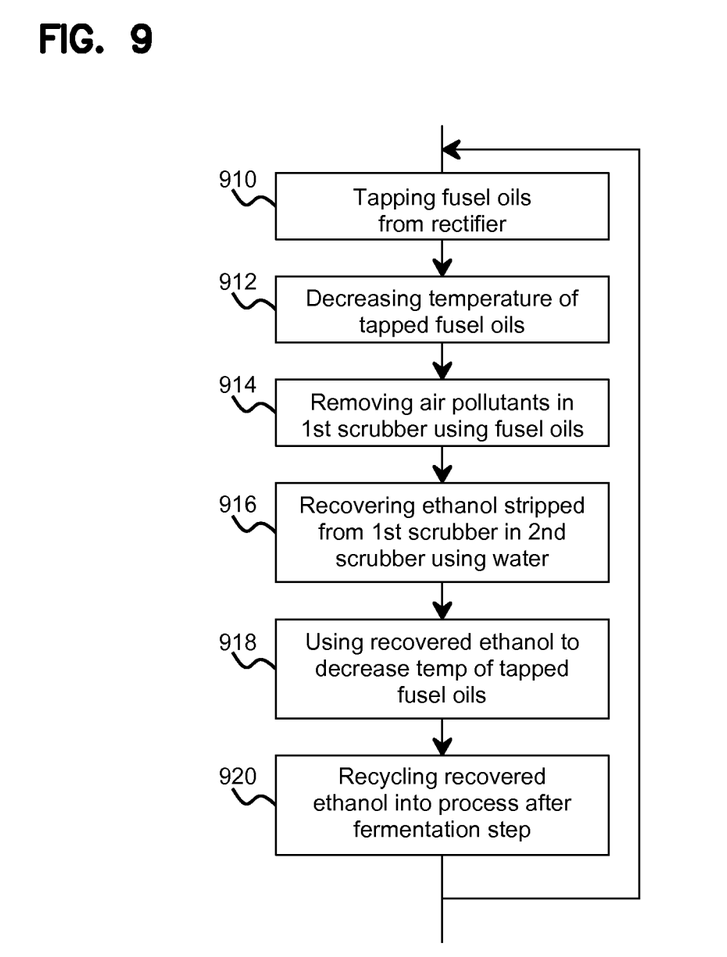
FIG. 9 is a flowchart of an ethanol recovery process according to the second exemplary embodiment of the present invention.

According to the second embodiment of the present invention, a procedure of recovering ethanol from fusel oils in an ethanol production process, as shown in FIG. 9, is as follows:

tapping fusel oil produced and trapped in the rectifier column 222 (step 910). Ethanol and water are also tapped together with the fusel oil;

decreasing the temperature of the tapped fusel oil blend in the heat exchanger 232 (step 912);

removing air pollutants produced under the fermentation process in the first scrubber 230 using the tapped fusel oil blend as scrubber solvent (step 914);

recovering ethanol using water as scrubbing solvent in the second scrubber 240 (step 916);

using the recovered ethanol blended with water to decrease the temperature of the tapped fusel oils in step 912 in the heat exchanger 232 (step 918), which increases the temperature of the recovered ethanol/water mix;

recycling the recovered ethanol into the process after the fermentation process (step 920), such as into the beer well 215.

The two stage scrubbing processes described above may be implemented in any existing plant producing ethanol used for fuel or beverage. The scrubbers are described as packed bed scrubbers herein, but any type of scrubbers can be used, such as tray scrubbers, venturi scrubbers and quencher scrubbers or a combination thereof.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of recovering ethanol from fusel oils in an ethanol production process, the method comprising:
   fermenting a mashed feedstock to produce a beer product, ethanol and air pollutants;
   distilling the beer product to produce ethanol and fusel oils, wherein the fusel oils comprise additional ethanol;
   tapping the fusel oils from the distilling step;
   using the tapped fusel oils in a first scrubber to remove the air pollutants produced during the fermenting step;
   recovering the ethanol produced by the fermenting step and the additional ethanol contained in the tapped fusel oils by the first scrubber; and
   recovering the ethanol recovered from the first scrubber in a second scrubber using water.

2. The method of claim 1, further comprising recycling the additional ethanol recovered in the second scrubber into the ethanol production process following the fermenting step and prior to the distilling step.

3. The method of claim 1, further comprising decreasing a temperature of the tapped fusel oils before using the tapped fusel oils in the first scrubber.

4. The method of claim 3, further comprising using the ethanol recovered in the second scrubber to decrease the temperature of the tapped fusel oils in a heat exchanger.

5. The method of claim 1, further comprising increasing a temperature of the ethanol recovered in the second scrubber using the tapped fusel oils in a heat exchanger.

6. The method of claim 1, further comprising recycling the water used to recover the ethanol recovered by the first scrubber in the second scrubber.

7. The method of claim 1, wherein the fusel oils are periodically tapped at various locations along a column used for the distilling step.

8. An improvement to an ethanol production process, wherein the process is conducted in a system comprising:
   a fermenter comprising a beer product line and a vented gas line configured to ferment a mashed feedstock into a beer product and producing ethanol and air pollutants;
   a distillation column operatively connected to the beer product line and comprising at least one fusel oil side tap configured to distill the beer product into ethanol and producing fusel oils comprising additional ethanol;
   a first scrubber operatively connected to the vented gas line; and
   a second scrubber operatively connected to the first scrubber;
   the improvement comprising:
      the first scrubber being configured to remove the air pollutants produced by the fermenter and to recover the ethanol produced by the fermenter and the additional ethanol in the fusel oils produced by the distillation column using a scrubber solvent including the fusel oils produced by the distillation column; and
      the second scrubber being configured to receive and recover the ethanol recovered by the first scrubber using water as a scrubber solvent.

9. An ethanol production system comprising:
   a fermenter comprising a beer product line and a vented gas line configured to ferment a mashed feedstock into a beer product and producing ethanol and air pollutants;
   a distillation column operatively connected to the beer product line and comprising at least one fusel oil side tap configured to distill the beer product into ethanol and producing fusel oils comprising additional ethanol;
   a first scrubber operatively connected to the at least one fusel oil side tap and operatively connected to the vented gas line configured to remove the air pollutants produced by the fermenter and to recover the ethanol produced by the fermenter the additional ethanol in the fusel oils produced by the distillation column using a scrubber solvent including the fusel oils produced by the distillation column; and
   a second scrubber operatively connected to the first scrubber receiving and recovering the ethanol recovered by the first scrubber using water as a scrubber solvent.

10. The ethanol production system of claim 9, further comprising a beer well configured to store the beer product produced in the fermenter and to receive ethanol recovered by the second scrubber.

11. The ethanol production system of claim 9, further comprising a heat exchanger arranged between the distillation column and the first scrubber decreasing a temperature of the fusel oils before using the fusel oils in the first scrubber.

12. The ethanol production system of claim 11, wherein the heat exchanger uses the ethanol recovered by the second scrubber to decrease the temperature of the fusel oils in the heat exchanger.

13. The ethanol production system of claim 9, further comprising a heat exchanger arranged between the distillation column and the first scrubber increasing a temperature of the ethanol recovered by the second scrubber using the fusel oils produced by the distillation column.

14. The ethanol production system of claim 9, further comprising a circuit recycling the water used to recover ethanol in the second scrubber back into the second scrubber.

15. The ethanol production system of claim 9, further comprising one or more valves arranged on the distillation column for periodically tapping the fusel oils produced by the distillation column.

16. The ethanol production system of claim 9, further comprising two or more valves arranged on the distillation column for periodically tapping the fusel oils produced by the distillation column at various locations along the distillation column.

* * * * *